United States Patent [19]

Ishihara et al.

[11] Patent Number: 5,273,753
[45] Date of Patent: Dec. 28, 1993

[54] EDIBLE COMPOSITION CONTAINING A POLYSACCHRIDE-PRODUCING ENZYME

[75] Inventors: Kazuoki Ishihara, Sagamihara; Masao Takahashi, Hachioji, both of Japan

[73] Assignee: Kabushiki Kaisha Advance, Tokyo, Japan

[21] Appl. No.: 730,884

[22] PCT Filed: Dec. 10, 1990

[86] PCT No.: PCT/JP90/01607
§ 371 Date: Jul. 19, 1991
§ 102(e) Date: Jul. 19, 1991

[87] PCT Pub. No.: WO91/08679
PCT Pub. Date: Jun. 27, 1991

[30] Foreign Application Priority Data

Dec. 11, 1989 [JP] Japan ................... 1-318934

[51] Int. Cl.⁵ .............. A61K 37/52; A61K 9/28; A23K 1/165; C12N 9/54
[52] U.S. Cl. ................... 424/439; 424/94.5; 424/440; 424/441; 424/442; 424/405; 424/407; 424/408; 424/410; 424/484; 424/486; 424/488; 424/474; 514/835; 514/944; 514/948; 514/960; 435/221; 435/222; 435/225; 530/825

[58] Field of Search .......... 424/94.5, 422, 434, 424/435, 439, 440, 441, 442, 405, 407, 408, 410, 484, 486, 488, 499, 490, 474; 514/835, 944, 948, 951, 960; 435/221, 222, 225; 530/825

[56] References Cited

U.S. PATENT DOCUMENTS 4,255,414  3/1981  Lembke et al. ............... 424/50

FOREIGN PATENT DOCUMENTS 0241441 10/1987 European Pat. Off. .
1602255 11/1970 France .
54-117038 9/1979 Japan .
0166981 10/1982 Japan .
57-166981 10/1982 Japan .

OTHER PUBLICATIONS

World Patents Index Latest, Section Ch. Week 8344, 1983, Derwent Pub. Ltd., London, GB; Class B, AN 83-805305 & JPA58162292 Abstract.
World Patents Index Latest, Section Ch. Week 8803, 1988, Derwent Pub. Ltd., London, GB; Class B, AN 88-017459 & JPA62278983 Abstract.

Primary Examiner—Paul R. Michl
Assistant Examiner—C. Azpuru
Attorney, Agent, or Firm—Finnegan, Henderson, Farabow, Garrett & Dunner

[57] ABSTRACT

A functional food which comprises a glucosyltransferase and/or a fructosyltransferase each having a water-soluble polysaccharide production ability, and a base therefor.

3 Claims, No Drawings

EDIBLE COMPOSITION CONTAINING A POLYSACCHRIDE-PRODUCING ENZYME

TECHNICAL FIELD

The present invention relates to a novel functional food or edible composition having a calorie intake lowering function.

BACKGROUND ART

Polysaccharide-producing enzyme (glycosyltransferases) such as glucosyltransferase(GT) and fructosyltransferase(FT) are previously utilized for, for example, the industrial production of dextran, but since this polysaccharide-producing enzyme has, in relation to living bodies, a plaque formation ability in the oral cavity, they have been regarded as the most important pathogenic factor of dental caries, and therefore, their utilization has been limited.

DISCLOSURE OF THE INVENTION

The object of the present invention is to provide a functional food or edible composition having a calorie intake lowering function.

According to the present invention, there is provided a functional food composition comprising at least one polysaccharide-producing enzyme selected from the group consisting of glucosyltransferases and fructosyltransferase having a water soluble polysaccharide production ability, and a base therefor.

BEST MODE OF CARRYING OUT THE INVENTION

As a result of intensive studies, the present inventors found that, when a water-soluble enzyme having a polysaccharide production capability is selected from the polysaccharide-producing enzymes, it does not become a dental caries pathogenic factor and forms polysaccharide from sucrose in the digestive tract to lower the calorie intake, and thus there can be provided a food or edible composition useful for the prophylaxis of adult disease factors such as obesity.

The constitution and effects, etc., of the invention are described in detail below.

ORIGIN OF THE ENZYMES

The enzymes GT and FT can be produced by the following bacteria. Examples of such bacteria are lactic acid bacteria (*Streptcoccus salivarius, S. bovis* and *S. sunguis*), *Bacillus natto* (*Bacillus subtilis*), molds (*Aspergillus niger, Aspergillus oryzae, Aureobasidum pullulans*), and plants (onion: *Arium sepa*). The following strains are exemplified as particularly useful: *B. subtilis* IAM 1168, *S. salivarius* ATCC 9758, *S. bovis* ATCC 9809, *A. pullulans* IAM 5060, *Asp. niger* ATCC 10864 and *Asp. oryzae* ATCC 1011.

CONSTITUTION OF THE EDIBLE COMPOSITION

When the above enzyme is orally ingested, the activity thereof is reduced by a digestive fluid such as the gastric juices, and to prevent this, the present composition can be constituted in usual enteric dosage forms such as gelatin capsules, or granules, or tablets coated with hydroxypropyl methyl cellulose or the like; gel-like dosage forms such as sodium alginate capable of reducing the gastric juice effect; and fat and oil-like dosage forms.

The amount of the polysaccharide or oligosaccharide-producing enzyme formulated in the edible composition according to the present invention varies depending upon, for example, the use and dosage form thereof, and is not particularly limited.

Bases used in edible compositions according to the present invention vary depending upon the forms of the compositions, and in addition to the case whereby the enzyme is added as it is, for example, in the case of a gel-like dosage form, there can be used a base obtained by dissolving the enzyme in a mixed solution of sodium alginate (0.2 to 2%), agar (0 to 5%) and gelatin (0 to 15%) and allow the solution to be gelled by cooling or drying, or a base obtained by drying the gelled product. On the other hand, in the case of a fat and oil-like dosage form, a fat and oil having a freezing point of 37° C. or more, for example, a hydrogenated oil of a vegetable fat and oil such as rapeseed oil (a fat or oil having a freezing point of 37° to 70° C. is obtained according to the degree of hydrogenation) is used. The fat and oil is heated and melted, the enzyme is then added at 1/20 to the equal weight, based upon the fat and oil, and the mixture is mixed and coagulated to obtain a fat and oil dosage form. As another dosage form, there can be mentioned the enzyme coated with an enteric material such as hydroxypropyl methyl cellulose or zein, i.e., a granule or tablet of the enzyme coated therewith, in which the enteric material is used in 1/20 to equal weight based upon the enzyme in the case of a coated granule and in an amount of 0.5 to 3% of a tablet in the case of a tablet. Further, in foods containing much animal protein including milk, the high pH buffering ability thereof can inhibit the gastric acidity, and thus there can be mentioned the addition of the enzyme into such foods or meat products after cooking.

Components appropriately formulated into ordinary foods such as, for example, starches, powder milk or other milks or milk products, casein, soybean protein, seasonings such as amino acids, chocolate raw materials, flour, perfumes and coloring matters can be compounded as optional components into the edible composition of the present invention.

OTHER PHYSIOLOGICAL EFFECTS

Foods or edible compositions according to the present invention have, in addition to the calorie intake lowering function, a selective proliferation effect on the intestinal useful bacteria due to the produced polysaccharides or oligosaccharides. Namely, for example, the polysaccharides and the like by the *S. salivarius*-derived enzyme can selectively proliferate *S. salivarius, S. bovis* and *L. acidophilus,* and oligosaccharides mainly bacteria of the genus *Bifidobacterium.*

EXAMPLES

The present invention is described in more detail below with reference to the following Examples, which by no means limit the scope of the present invention.

Example 1: Preparation of a polysaccharide-producing enzyme

*S. salivarius* ATCC 9758 is given as an example.

The ATCC 9758 strain was inoculated with an initial viable cell count of $10^6$/ml into a SYPT medium (10% sucrose, 1% yeast extract, 1% peptone, 0.1% Tween 80) and cultured at a temperature of 37° C. and a pH of 7.0 under an aerobic condition.

A dropwise addition of a 5N NaOH solution prevented the pH lowering accompanying lactic acid fermentation, and the pH of the system was maintained at a constant value. After 7 hours culturing, the culture broth was subjected, for example, to filtration with a membrane filter (0.1μ filter produced by ASAHI CHEMICAL INDUSTRY CO , LTD.) or centrifugation (10,000×g), and the resulting culture supernatant was concentrated and desalted by using an ultrafiltration membrane having a fractionation molecular weight of about 15,000 (produced by Mitsui Petrochemical Industries, Ltd). The concentration and desalting also can be carried out by adding ammonium sulfate to a 50% saturation thereof under ice cooling, centrifuging the mixture at 15,000×g, and dialyzing the precipitate using distilled water as an outer fluid. The yield of the enzyme preparation by the present method was about 2500 U or more per liter of the culture broth.

Example 2: Measurement of the activity of the polysaccharide-producing enzyme

A 10 mg amount of the enzyme preparation was dissolved in 1 ml of deionized water, 0.1 ml thereof was dissolved in 3.2 ml of a phosphate buffer (pH 6.0, 0.05M) containing 2% sucrose, an enzymatic reaction was carried out at 37° C. for 10 minutes, and 0.7 ml of a 2N NaOH solution was added to terminate the reaction.

The reaction solution was neutralized and dialyzed (the outer fluid was distilled water) at 60° C. for 20 hours, and the polysaccharide amount produced in the resulting reaction solution was determined by measuring the volume of the dialysis inner fluid and the polysaccharide concentration thereof by the phenol-sulfuric acid method, and multiplying the obtained values. The polysaccharide formation amount was determined by subtracting the polysaccharide amount before the 10 minutes reaction from the polysaccharide amount after the 10 minutes reaction. The 1U was defined as the enzyme preparation amount used for the formation of 1 mg of polysaccharide from sucrose, for 1 minute.

The weight of the serum triglyceride and fat tissues was measured when fructosyltransferase was ingested, together with sucrose, by rats. The results are shown below.

Influence of the fructosyltransferase (F Tase) agent on rat serum triglyceride and fat tissue weight

|  | Serum TG (mg/dl) | | Fat tissue weight |
|---|---|---|---|
|  | 3W | 4W |  |
| Normal diet group | 216 ± 19.5[a] | 200 ± 17.1 | 2.33 ± 0.14 |
| 40% sucrose diet group | 286 ± 20.6 ⎤* | 346 ± 50.1 ⎤* | 2.95 ± 0.09 ⎤* |
| 40% sucrose diet group +FTase group | 235 ± 11.4 ⎦ | 260 ± 25.4 ⎦ | 2.50 ± 0.21 ⎦ |

Rats (Wister, , 6 weeks old, 5 animals per group) were bred for 4 weeks under set diet conditions. A FTase enzyme preparation of about 680 U/g was added to 0.5% (1U is an enzyme amout required to form 1 g of the polysaccharides per one hour).

a) mean±S.E.

*) p<0.05

Example 3: Preparation of gel-like and fat and oil-like dosage forms

1. Gel-like dosage form

As hereinafter described, a jelly obtained by adding sodium alginate to agar gel effectively retains an enzymatic activity even under an acidic condition, and is useful for the protection of the enzyme from the gastric juice, similar to general enteric preparations. The base composition of the jelly with addition of alginic acid is given below.

| Sodium alginate | 1% (generally 0.5 to 2%) |
|---|---|
| Gelatin | 2% (generally 0 to 10%) |
| Agar | 1.3% (generally 0 to 2%) |
| Potassium phosphate | 1.5% (pH of 6.5 is obtained) |

(pH usually maintained at 5 to 7.5)

The activity expression of the polysaccharide-producing enzyme was not influenced by adding, as a sweetener, mannitol or xylose or another flavoring. The base was sufficiently melted at about 100° C. and was kept warm at about 45° to 50° C. The above enzyme preparation was added to this sol at a rate of 50 mg (12.5 U) per ml of the sol, and the mixture was mixed and allowed to cool to obtain a coagulated substance. This gel can further be air-dried overnight at room temperature to prepare a dried substance having an enzymatic activity.

2. Fat and oil-like dosage form

Hydrogenated oils having a melting point in the range of 38° to 70° C. have a coating effect and protect the polysaccharide-producing enzyme from the gastric juices. Particularly, hydrogenated oils having a melting point of 38° to 42° C., higher than the body temperature by 1° to 4° C., have the same effect in a jelly-like dosage form. A method of preparing a hydrogenated palm oil having a melting point of 38° C. is described herinafter as an example.

1 g of a hydrogenated palm oil (produced by NIPPON OIL AND FATS CO., LTD.) was melted by heating at a temparature of 45° C., 0.56 g (140 U) of the polysaccharide-producing enzyme was added, 90 mg of potassium phosphate was added, and the mixture was mixed and allowed to cool overnight at room or a low temperature, to be coagulated, whereby the desired fat and oil-like dosage form was obtained.

Example 4: Protection from gastric juices by gel-like and fat and oil-like dosage forms 1. Gel-like dosage form The activity of the polysaccharide-producing enzyme to be added to the base was measured before preparing a gel-like agent.

A physiological saline of pH 3.0 containing 0.1% pepsin (produced by Wako Pure Chemical Industries, Ltd.) was prepared as an artificial gastric juice, and to 1 l thereof were added 10 g (0.7 g as the dried jelly, 125 U), of the gel-like agent prepared in Example 3, and 40 g of sucrose. After one hour's shaking at 37° C., the pH was increased to 7.2 to 7.5 with a 2N NaOH aqueous solution, 0.1% pancreatin was added, and further, a total of two hours incubation was carried out. The polysaccharide formation amount was measured by sampling at intervals. This measurement was made by adding 0.5 ml of a 5N NaOH aqueous solution to 9.5 ml of the sampled fluid, to neutralize the same, and using the same method as the above activity measurement method. The formation of polysaccharides was not observed in the gel-like agent to which alginic acid was not added (Comparative Example). The results are shown in Table 1.

2. Fat and oil-like dosage form

A 1 g (90 U) amount of a fat and oil-like agent comprising the hydrogenated oil prepared in Example 3 and the polysaccharide-producing enzyme was added to an artificial gastic juice in the same manner as for the gel-like dosage form, and sampling at intervals and the measurement of the polysaccharide formation amount were carried out. The results are shown in Table 1.

TABLE 1

| | Polysaccharide formation amount in the artificial gastric juice (ml/l/U) | | |
|---|---|---|---|
| | Jelly-like agent | | Fat and |
| Sampling time (mt) | No addition of alginic acid | Addition of alginic acid | oil-like agent |
| 0 | 0.32 | 0.48 | 0.78 |
| 20 | 0.40 | 2.08 | 1.11 |
| 60 | 0.72 | 3.28 | 5.00 |
| 80 | 1.44 | 12.2 | 9.78 |
| 120 | 1.44 | 20.0 | 17.7 |

We claim:

1. An edible composition in gel dosage form comprising at least one polysaccharide or oligosaccharide-producing enzyme selected from the group consisting of glucosyltransferase and fructosyltransferase wherein said enzyme has the ability to produce a water-soluble polysaccharide from sucrose, and said enzyme being mixed in a base solution therefor containing 0.5 to 2% sodium alginate, 0 to 10% gelatin and 0 to 2% sodium.

2. An edible composition in granular form comprising at least one polysaccharide or oligosacharide-producing enzyme selected from the group consisting of glucosyltransferase and fructosyltransferase wherein said enzyme has the ability to produce a water-soluble polysaccharide from sucrose, and said enzyme being coated with an enteric material selected from the group consisting of hydroxypropyl methyl cellulose, carboxymethyl ethyl cellulose, zein, and shellac, wherein the enteric material is used in 1/20 to equal weight based upon the enzyme.

3. An edible composition in tablet form comprising at least one polysaccharide or oligosaccharide-producing enzyme selected from the group consisting of glucosyltransferase and fructosyltransferase wherein said enzyme has the ability to produce a water-soluble polysaccharide from sucrose, and said enzyme being coated with an enteric material selected from the group consisting of hydroxypropyl methyl cellulose, carboxymethyl ethyl cellulose, zein, and shellac, wherein the enteric material is used in an amount of from 0.5 to 3% based upon the enzyme.

* * * * *

UNITED STATES PATENT AND TRADEMARK OFFICE
CERTIFICATE OF CORRECTION

PATENT NO. : 5,273,753
DATED : December 28, 1993
INVENTOR(S) : Kazuoki ISHIHARA and Masao TAKAHASHI It is certified that error appears in the above-indentified patent and that said Letters Patent is hereby corrected as shown below:

On the title page, Item [54] and Col. 1, line 2, "POLYSACCHRIDE" TO
--POLYSACCHARIDE--.
Claim 2, column 6, line 7, change "oligosacaride" to
--oligosaccaride--.

Signed and Sealed this

Thirty-first Day of May, 1994

Attest:

BRUCE LEHMAN

*Attesting Officer*     *Commissioner of Patents and Trademarks*